US006919376B2

(12) United States Patent
Llompart et al.

(10) Patent No.: US 6,919,376 B2
(45) Date of Patent: Jul. 19, 2005

(54) THERAPEUTIC AGENTS AND CORRESPONDING TREATMENTS

(75) Inventors: Javier Llompart, Valencia (ES); Jorge Galvez, Valencia (ES)

(73) Assignee: Medisyn Technologies, Inc., Minnetonka, MN (US)

( * ) Notice: Subject to any disclaimer, the term of this patent is extended or adjusted under 35 U.S.C. 154(b) by 0 days.

(21) Appl. No.: 10/251,616

(22) Filed: Sep. 20, 2002

(65) Prior Publication Data

US 2004/0059000 A1 Mar. 25, 2004

(51) Int. Cl.[7] .......................... A01N 41/06; A61K 31/18
(52) U.S. Cl. ...................... 514/601; 514/511; 514/553; 564/80
(58) Field of Search ........................... 564/80; 514/601, 514/553, 511

(56) References Cited

U.S. PATENT DOCUMENTS

| | | | |
|---|---|---|---|
| 6,290,929 B1 | 9/2001 | Camden | 424/1.11 |
| 6,352,844 B1 | 3/2002 | Maurer et al. | 435/69.2 |

OTHER PUBLICATIONS

SIGMA, Biochemicals, Organic Compounds, Diagnostic Reagents, p. 340.*
Gerona–Navarro et al., General Approach for the Stereocontrolled Construction of the Beta–Lactam Ring in Amino Acid–Derived 4–Alkyl–4–carboxy–2–azetidinones, Journal of Organic Chemistry, 67, pp. 3953–3956, published on web Apr. 26, 2002.*
Hernanz et al., Synthesis and Configuration Assignment of (R) and (S)–2–bromohexadecanoic Acids, Tetrahedron: Asymmetry, vol. 6, No. 9 pp 2291–2298 (1995).*
Oppolzer et al., Asymmetric Diels–Alder Reactions: Facile Preparation and Structure of Sulfonamido–Isobornyl Acrylates, Tetrahedron Letters, vol. 25, No. 51 pp 5885–5888 (1984).*
Cativiela et al., "New Approaches to the Asymmetric Synthesis of ∝–Methylphenylalanie" Tetrahedron Letters, vol. 5, No. 2, pp. 261–268. (1994).
R. Ohme; H. Preuschhof. Liebigs Ann. Chem., "Hydrazine und Azoverbindungen aus Diamiden der Schwefelsaure", Justus Liebigs Annalen der Chemie, vol. 713, pp. 74–86.

Bermann, Manfred; Van Wazer, John R. Synthesis, "Preparation of N,N'–Dimethyl–and N,N'–Diethylsulfamid", Synthesis, vol. 10, pp. 576–577.
Oppolzer, W., "Chiral auxiliary conferring excellent diastereodifferentiation in reactions of O–enoyl and enolate derivatives," Tetrahedron, vol. 43, No. 9, pp. 1969–2004.
Oppolzer, W. and Moretti, R. "Enantioselective systheses of α–amino acids from 10–sulfonamido–isobornyl esters and di–t–butyl azodiacarboxylate", Tetrahedron, vol. 44, No. 17, pp. 5541–5552.
Gray, G. and Wickstrom, E., "Evaluation of Anchorage–Independt Proliferation in Tumorigenic Cells Using the Redox Dye alamarBlue™", Biotechniques, vol. 21, No. 5, pp. 780–782.
J. Gálvez, R. García–Domenech, C. de Gregorio Alapont, J.V. de Julián–Ortiz, and L. Popa, "Pharmacological distribution diagrams: A tool for de novo drug design", Journal of Molecular Graphics, vol. 14, pp. 272–276.
Boyd, M., MD, Ph.D., "The NCI In Vitro Anticancer Drug Discovery Screen" Anticancer Drug Development Guide, Preclinical Screening, Clinical Trials, and Approval, B. Teicher Humana Press, Inc. pp. 23–42.
Dewynter, G., Abdaoui, M., Toupet, L. and Montero, J., "Sulfonyl Bis–N–Oxazolidinone (SBO): A New Versatile Dielectrophile with Sequential Reactivity", Tetrehedron Letters, vol. 38, No. 50, pp. 8691–8694.
Gong, B.; Zheng, C.; Skrzpczak–Jankun, E.; Yan, Y.; Zhang, J.; "A Robus Two–Dimensional Hydrogen–Bonded Network: The Sulfamide Moiety as a New Builidng Block for the Design of Molecular Solids", J. Am. Chem. Soc., vol. 120, No. 43, pp. 11194–11195.
Gong, B.; Zheng, C.; Zeng, H.; Zhu, J., "Polar Assembly of N,N'–Bis(4–substituted benzyl)sulfamides", J. Am. Chem. Soc., vol. 121, pp. 9766–9767.
Nuckolls C., Hof, F.; Martin, T.; Rebek J. Jr.; "Chiral Microenvironments in Self–Assembled Capsules", J. Am. Chem. Soc., vol. 121, pp. 10281–10285.

* cited by examiner

Primary Examiner—Frederick Krass
Assistant Examiner—Amy Lewis
(74) Attorney, Agent, or Firm—Patterson, Thuente, Skaar & Christensen, P.A.

(57) ABSTRACT

Compositions and methods of using an MT103 family member, wherein MT103 is the chemical N,N-dicyclohexyl-(1S)-isoborneol-10-sulfonamide. Uses of the compositions include cancer therapy, antibacterials, antifungals, induction of apoptosis, and hormonal antagonists.

44 Claims, 11 Drawing Sheets

N,N-dicyclohexyl-2-hydroxy-7,7-dimethylbicyclo[2.2.1]hept-1-ylmethanesulfonamide N,N-diisopropyl-2-hydroxy-7,7-dimethylbicyclo[2.2.1]hept-1-ylmethanesulfonamide N,N-dimethyl-2-hydroxy-7,7-dimethylbicyclo[2.2.1]hept-1-ylmethanesulfonamide N-cyclohexyl-N-(3,4-dimethylcyclohexyl)-2,3-dihydroxy-7,7-dimethylbicyclo[2.2.1]hept-1-ylmethanesulfonamide N1-cyclohexyl-N1-{4-[(E)ethylidene]-3-methylenecyclohexyl}-1-(2-hydroxy-7,7-dimethylbicyclo[2.2.1]hept-1-yl)-1-ethylenesulfonamide 4-cyclohexyl[1-(2-hydroxy-7,7-dimethylbicyclo[2.2.1]hept-1-yl)vinyl]sulfonamido-2-methyl-1,3-cyclohexanedicarboxylic acid 4-[3,4-dihydroxycyclohexyl(2-hydroxy-7,7-dimethyl bicyclo[2.2.1]hept-1-ylmethyl)sulfonamido]-2-methyl-1,3-cyclohexanedicarboxylic acid The basic synthesis pathway is the typical for sulfonamides:

THERAPEUTIC AGENTS AND CORRESPONDING TREATMENTS

FIELD

The application is generally related to methods of treating cancer and methods of inhibiting cell growth.

BACKGROUND

Cancer is a disease that afflicts many people and is a leading cause of death in humans and non-human animals. Cancers typically involve cells that grow by uncontrolled growth of the cells that creates many new cells. Many anti-cancer drugs are agents that inhibit or stop cell growth.

Many anti-cancer drugs are known to be effective against cancers and tumor cells, but some cancers and tumors respond poorly to these drugs. Further, many anti-cancer drugs also destroy other cells in the body. Thus new anti-cancer drugs are required, and drugs that are able to target specific cancer types are desirable.

Agents that inhibit cell growth are useful as anti-cancer drugs. The National Cancer Institute (NCI) is an agency of the United States government that is involved in the testing of anti-cancer drugs. NCI often conducts screening tests of potential anti-cancer drugs using a three cell line test. Each of the three cell lines is a type of cancerous cell. The cells are exposed to the drug candidates, and the drugs' effectiveness in stopping cell growth and/or killing the cells is measured.

The NCI typically tests the most promising drugs with a further battery of approximately 60 cell lines, and the dose of the drug that is required to stop cell growth and to kill cells is measured. The dose of the drug that is required to inhibit approximately 50% of the growth of a cancer cell is reported as the $GI_{50}$ concentration of the drug. The lower the $GI_{50}$, the more effective is the anti-cancer drug. The $GI_{50}$ is sometimes reported in the units of $-\log (GI_{50})$, so that the higher the value for $-\log (GI_{50})$, the more effective is the anti-cancer drug. The dose of the drug that is required to stop approximately 100% of cell growth is reported as the total growth inhibition (TGI) concentration of the drug. The dose of the drug that is required to reduce the number of the cells to 50% of the original number of cells is referred to as the $LC_{50}$ concentration. The lower the TGI or $LC_{50}$, the more potent is the anti-cancer drug.

The creation of new anti-cancer drugs is a challenging process. An important step is the selection of drug candidates for initial screening. Many approaches for selecting these drug candidates are used. One approach is to use computer modeling to design molecules that have physicochemical properties that are useful as anti-cancer agents.

SUMMARY OF THE INVENTION

The invention includes embodiments related to the MT103 family of therapeutic compounds, as shown for example, in FIGS. 1–8. An embodiment of the invention is a method of using the compounds depicted in FIGS. 1–8 for treatment of patients, for example, as a cancer therapeutic, and as antibacterials, antifungals, apoptosis agents, and hormonal antagonists.

Embodiments of the invention include methods for treating a patient, including administering to the patient a therapeutically effective amount of a composition comprising a chemical having the formula depicted in FIG. 8, with $R_1$, $R_2$, $R_3$, $R_4$, and $R_5$ being independently chosen from the group consisting of H, OH, $C_1$–$C_3$ alkyl, a halogen, primary amine, secondary amine, tertiary amine, carboxy, alkoxy, alkyoxycarbonyl, carboxamido, and $C_1$–$C_3$ alkenyl; with $R_6$ and $R_7$ being independently chosen from the group consisting of H, $C_1$–$C_3$ alkyl, and $C_1$–$C_3$ alkenyl, and with $R_8$ and $R_9$ being independently chosen from the group consisting of chemical groups having 1 to 12 carbons. In other embodiments, $R_8$ and $R_9$ are independently chosen from the group consisting of $C_1$–$C_4$ alkyl, $C_1$–$C_4$ alkenyl, $C_3$–$C_6$ cycloalkyl, $C_3$–$C_6$ cycloalkenyl, and $C_6$ cycloalkyls derivitized with at least one member of the group consisting of $C_1$–$C_4$ alkyl, $C_1$–$C_4$ alkenyl, hydroxyl, and carboxyl.

DETAILED DESCRIPTION OF THE PREFERRED EMBODIMENTS

Figure 1:
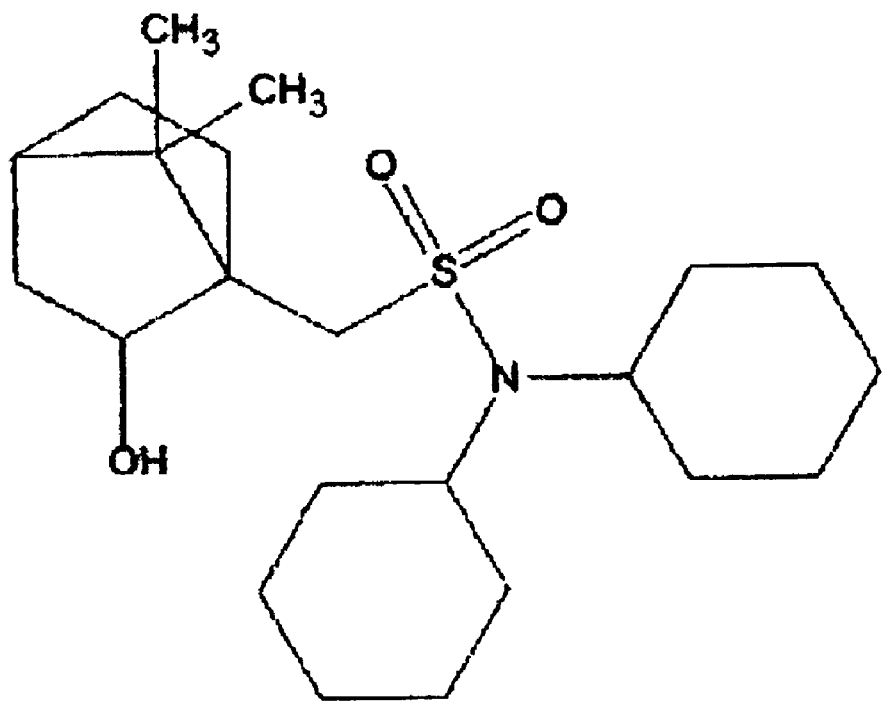
FIG. 1 depicts the chemical structure of a member of the MT103 family, N,N-dicyclohexyl-2-hydroxy-7,7-dimethylbicyclo[2.2.1]hept-1-ylmethanesulfonamide (also known as: MT103 or N,N-dicyclohexyl-(1S)-isoborneol-10-sulfonamide)
Figure 2:
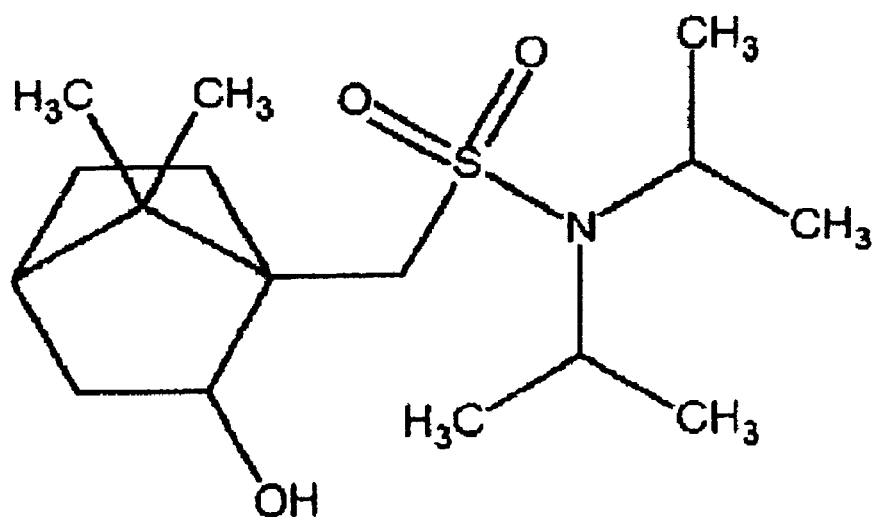
FIG. 2 depicts the chemical structure of a member of the MT103 family, N,N-diisopropyl-2-hydroxy-7,7-dimethylbicyclo[2.2.1]hept-1-ylmethanesulfonamide.
Figure 3:
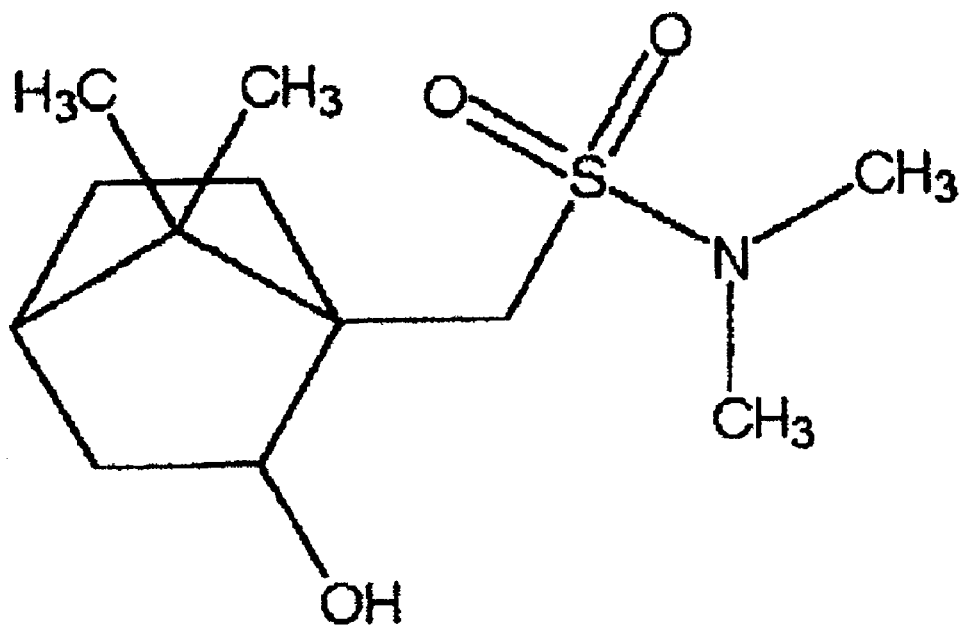
FIG. 3 depicts the chemical structure of a member of the MT103 family, N,N-dimethyl-2-hydroxy-7,7-dimethylbicyclo[2.2.1]hept-1-ylmethanesulfonamide.
Figure 4:
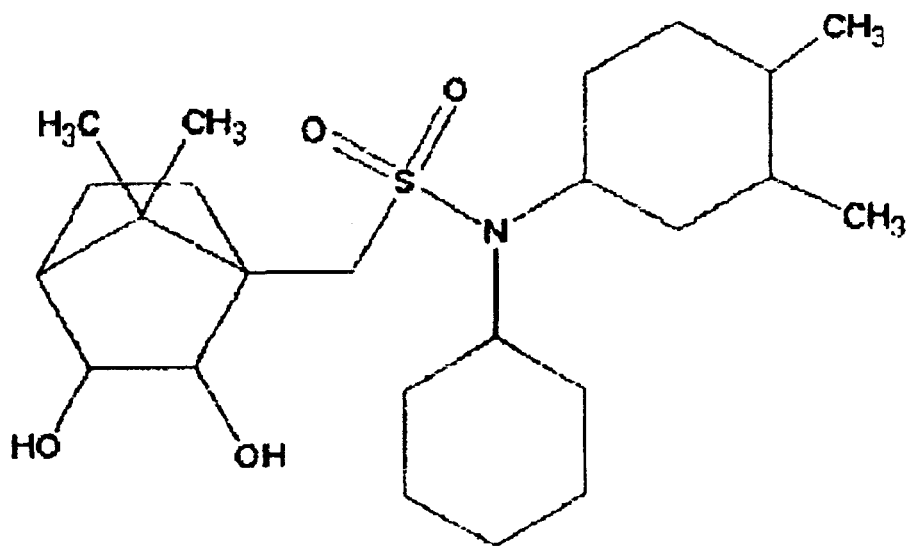
FIG. 4 depicts the chemical structure of a member of the MT103 family, N-cyclohexyl-N-(3,4-dimethylcyclohexyl)-2,3-dihydroxy-7,7-dimethylbicyclo[2.2.1]hept-1-ylmethanesulfonamide.
Figure 5:
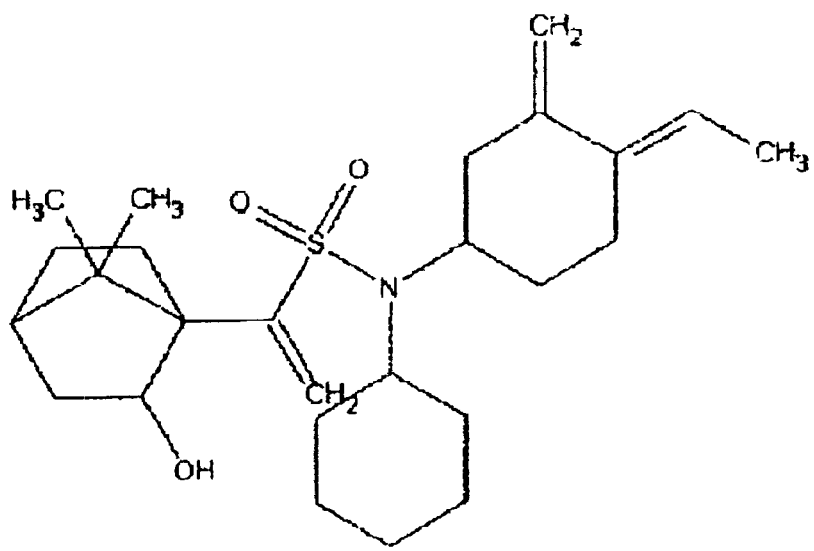
FIG. 5 depicts the chemical structure of a member of the MT103 family, N1-cyclohexyl-N-1-{4-[(E)ethylidene]-3-methylenecycolhexyl}-1-(2-hydroxy-7,7-dimethylbicyclo[2.2.a]hept-1-yl)-1-ehtylenesulfonamide.
Figure 6:
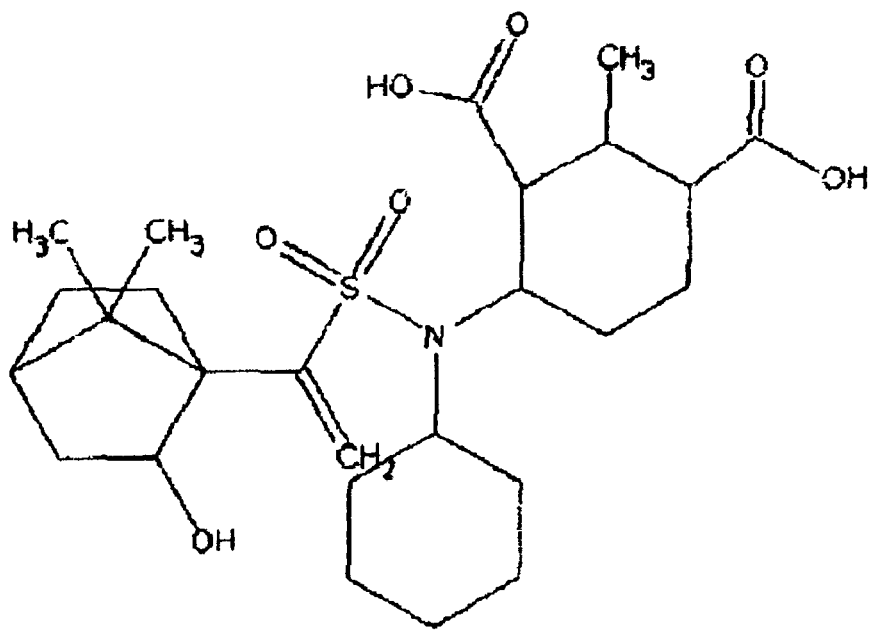
FIG. 6 depicts the chemical structure of a member of the MT103 family, 4-cyclohexyl[1-(2-hydroxy-7,7-dimethylbicyclo[2.2.1]hept-1-yl)vinyl]sulfanamido-2-methyl-1,3-cyclohexanedicarboxylic acid.
Figure 7:
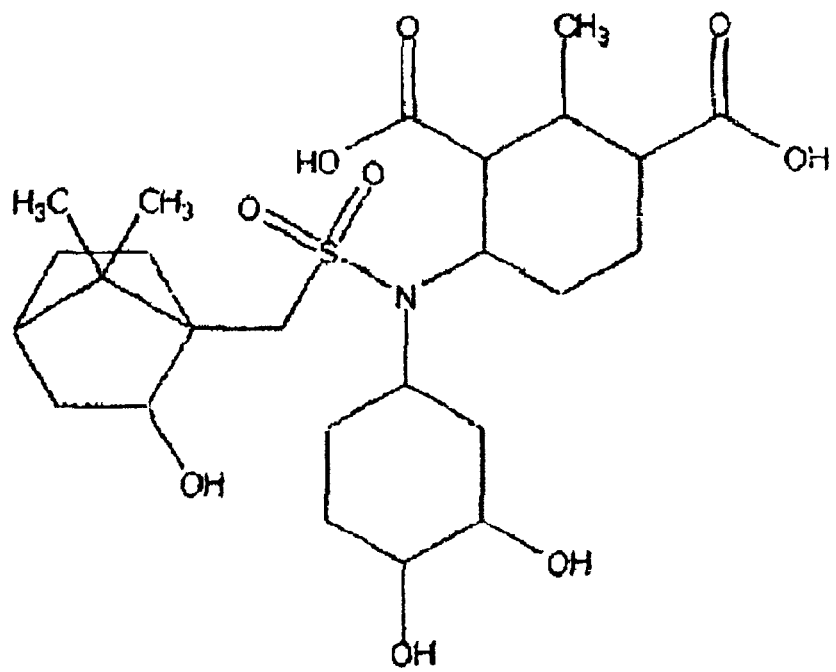
FIG. 7 depicts the chemical structure of a member of the MT103 family, 4-[3,4-dihydroxycyclohexyl(2-hydroxy-7,7-dimethylbicyclo[2.2.1]hept-1-ylmethyl)sulfonamido]-2-methyl-1,3-cyclohexanedicarboxylic acid.
Figure 8:
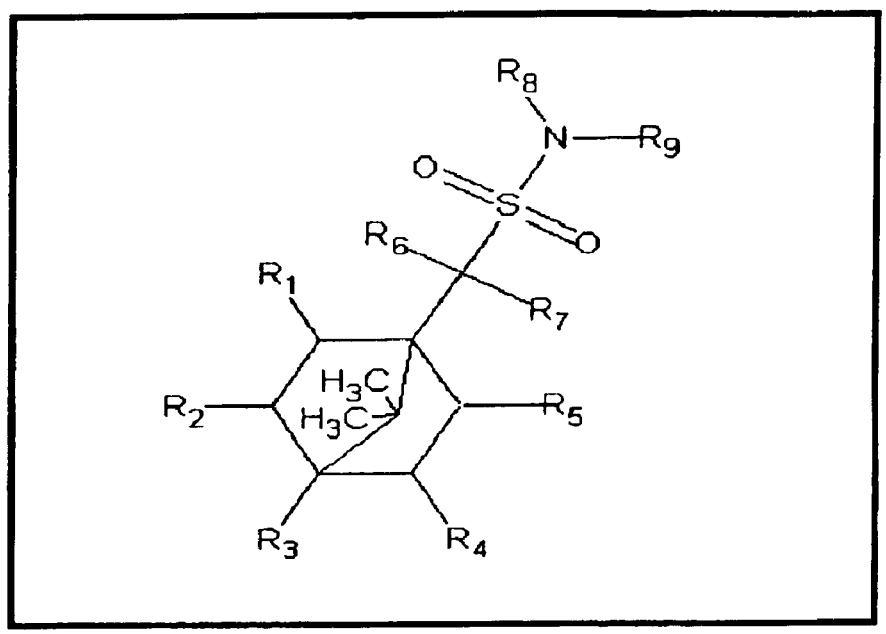
FIG. 8 depicts a chemical structure outlining the general features of the MT103 family.

An embodiment of the invention is a family of drugs, referred to herein as the MT103 family, that is bioactive, affects cellular functions, and inhibits cancer. A species of this family is N,N-dicyclohexyl-(1S)-isoborneol-10-sulfonamide, also referred to herein as MT103, which is depicted in FIG. 1. Other members of the MT103 family of drugs are depicted in FIGS. 2–7. FIG. 8 depicts the overall general structure of the MT103 family. MT103 was discovered to be an anticancer agent using a topological computer model. MT103 was tested by the NCI and shown to be an effective anti-cancer drug and an effective inhibitor of cell growth, as described in detail in the Examples below. The same model shows that the MT103 family is generally bioactive and inhibitory of cancer, especially non-small cell lung cancer.

Non-small lung cancer is a type of lung neoplasm. In fact, 95% of primary lung neoplasms are bronchogenic carcinoma/epithelial neoplasms. Bronchogenic carcinoma is commonly divided into two groups: small cell lung cancer, which accounts for about 20% of all cases; and non-small cell lung cancer, which accounts for about 80% of all cases. The non-small cell lung cancer group is further divided into 3 tumor categories based on cell morphology. One category is Squamous cell carcinoma (also called epidermoid carcinoma), which accounts for about 40% of non-small cell lung cancer cases. The second category is Adenocarcinoma, which accounts for 45% of all cases and is the most common lung cancer in non-smokers. The remaining 10% of cases are Large cell lung cancers, which are rapidly fatal.

As shown in the Examples, MT103 has demonstrated activity against all three categories of non-small cell lung cancer, as demonstrated by tests with multiple cells, including HOP-92 cells (Large cell model), NCI-H460 (Large cell model), NCI-H522 (Adenocarcinoma model), and NCI-H226 cell line (Squamous cell model). The tests show activity for all 3 primary non-small cell lung cancer tumor types. These tests are described further in the example below.

MT103 is effective against cancer cells in general and is particularly effective against non-small lung cancer cells. In fact, MT103 has a -logGI$_{50}$ value of 5.6 as tested by the NCI in the HOP-92 non-small lung cancer cell line, a large value that indicates that MT103 is particularly effective against this type of cancer. The members of the MT103 family that share motifs of MT103 are therefore also expected to have the anti-cancer function of MT103, as well as its mode of action, and other functions.

Computer modeling and comparison to other chemicals shows that MT103 and the MT103 family are anti-cancer agents, inducers of apoptosis agents, hormonal antagonists, antibacterials, antifungals, and hypolipidemic. Some chemicals used for such comparisons are tamoxifen, anastrozole, and flutamide.

Since the MT103 family of drugs generally have these characteristics, they may be used to treat patients to inhibit cancer and to act in the patients as apoptosis agents, hormonal antagonists, antibacterials, antifungals, and hypolipidemic. Cells in vitro and in vivo may be exposed to members of the MT103 family for this purpose. MT103 and the MT103 family are useful not only as drugs for treating or curing certain cancer types but also as drugs that inhibit certain cancer types in humans and non-human animals. Further, apoptotic agents, hormonal antagonists, antibacterials, and antifungals are important commercial products that are used in many ways; similarly, members of the MT103 family may also be used for such purposes.

Hypolipidemic drug therapy is used in cases of hyperlidemia (hypercholesterolemia) to reduce cholesterol levels. These drugs have been used in well-controlled studies of patients with high cholesterol levels caused primarily by elevated levels of low-density lipoproteins (LDL). The results of these trails indicate that coronary heart disease (CHD) mortality is reduced by as much as 30% to 40% and that nonfatal events are similarly reduced when hypercholesterolemic patients are treated with moderate doses of hypolipidemic drugs [Scandinavian Simvastatin Survival Study Group, 1994: Shepard et al., 1995; The Long-Term Intervention with Pravastatin in Ischaemic Disease (LIPID) Study Group, 1998].

Further, the MT103 family of chemicals may be used in vitro or in vivo to slow or stop cell growth, kill cells, or to inhibit the growth of cells in vitro or in vivo. Apoptosis inductors and hormonal antagonists are valuable research tools for in vitro and in vivo treatment of cells. Antibacterials and antifungals are valuable products for suppressing, inhibiting and/or killing bacteria and fungi in vitro, in vivo, ex vivo, in humans, in non-humans, and in a multitude of environments such as residential, commercial, hospital, and industrial settings. These compounds may be used alone or in combination with other drugs to achieve the most suitable therapy for a patient or other purposes.

Many compounds of this invention are most preferable for use in certain types of cancer but are also useful in the treatment of a variety of cancers including, but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma. According to another embodiment of the invention, compounds of the invention are directed to therapies for cell proliferative disorders, for example, Alzheimer's disease, viral infections, auto-immune diseases and neurodegenerative disorders.

MT103 and the MT103 family are also useful when delivered in combination with medical devices, for example, stents for use in blood vessels or other portions of the body, heart valves, pacemakers, defibrillators, angioplasty devices, artificial blood vessels, artificial hearts, catheters, indwelling and temporary catheters, devices deployed temporarily, permanently, or semi-permanently in contact with blood, oxygenator lines, blood pumps, blood filters, sensors, biosensors, diagnostic kits, devices that contact blood, drug delivery systems, and medical implants. One function of MT103 family compounds is to inhibit cell growth around an implanted device. The inhibition may be for a short time, for example while the body's inflammatory reaction is most active, on a longer term basis, or permanent. The inhibition of cell growth is a significant strategy for the prevention of restenosis after angioplasty or implanting a stent in a blood vessel. Inhibition of cell growth is also a significant strategy for enhancing the biocompatibility of implanted devices so that the reaction of the body to the devices is minimized.

FIG. 8 shows motifs for the MT103 family. The motif of FIG. 8 has been found to be significant with respect to therapeutic function by computer modeling. $R_1$, $R_2$, $R_3$, $R_4$, and $R_5$ are independently chosen from the group consisting of H, OH, halogens (such as F, Cl, Br, and/or I), $C_1$–$C_3$ alkyl, primary amines, secondary amines, tertiary amines, carboxy groups, ether (alkoxy) groups, ester (alkoxycarbonyl) groups, amide (carboxamido) groups and $C_1$–$C_3$ alkenyl; $R_6$ and $R_7$ are independently chosen from the group consisting of H, $C_1$–$C_3$ alkyl, and $C_1$–$C_3$ alkenyl, and $R_8$ and $R_9$ are independently chosen from the group consisting of chemical groups having 1 to 12 carbons. In some embodiments, species in the MT103 family are characterized by the independent choice of $R_8$ and $R_9$ from the group consisting of $C_1$–$C_4$ alkyl, $C_1$–$C_4$ alkenyl, $C_3$–$C_8$ cycloalkyl, $C_3$–$C_8$ cycloalkenyl, and $C_6$ cycloalkyls derivitized with at least one member of the group consisting of $C_1$–$C_4$ alkyl, $C_1$–$C_4$ alkenyl, hydroxyl, and carboxyl. The use of any combination of the chemical groups described herein for $R_1$ to $R_9$ and for the derivitization of $C_6$ groups in the $R_8$ and $R_9$ positions are believed to result in chemicals having the functions of MT103, as are the stereoisomers thereof. The stereoisomers of the structures depicted by FIGS. 1–8 are members of the MT103 family and are expected have the functions of MT103. As used herein, the notation $C_n$ indicates a chemical or chemical group having n Carbon atoms.

Some chemical groups in MT103 family are believed to be preferable, although other members of the family may have desirable characteristics also. These include hydrogens or short alkyls or alkenyls, particularly methyls, at $R_6$ and $R_7$. The $C_6$ cycloalkyls or their derivatives are considered to be preferable at $R_8$ and $R_9$. In particular, for $R_8$ and $R_9$ such $C_6$ derivatives that have hydroxyls or carboxyls on at least two positions of the $C_6$ are preferable: indeed, the compounds represented in FIGS. 6 and 7 are predicted by computer modeling to have an enhanced activity compared to MT103. In contrast, the MT103 family member depicted in FIG. 3, which has methyl groups at $R_8$ and $R_9$, is predicted to have a generally lower activity compared to MT103. The presence of at least one hydroxyl in positions $R_1$ to $R_5$ is also believed to be preferable but not essential for function.

Species of the MT103 family include, for example, N,N-dicyclohexyl-(1S)-isoborneol-10-sulfonamide, N,N-diisopropyl-2-hydroxy-7,7-dimethylbicyclo[2.2.1]hept-1-ylmethanesulfonamide, N,N-dimethyl-2-hydroxy-7,7-dimethylbicyclo[2.2.1]hept-1-ylmethanesulfonamide, N-cyclohexyl-N-(3,4-dimethylcyclohexyl)-2,3-dihydroxy-7,7-dimethylbicyclo[2.2.1]hept-1-ylmethanesulfonamide, N1-cyclohexyl-N1-{4-[(E)ethylidene]-3-methylenecycolhexyl}-1-(2-hydroxy-7,7-dimethylbicyclo[2.2.1]hept-1-yl)-1-ethylenesulfonamide, 4-cyclohexyl[1-(2-hydroxy-7,7-dimethylbicyclo[2.2.1]hept-1-yl)vinyl]sulfanamido-2-methyl-1,3-cyclohexanedicarboxylic acid, 4-[3,4-dihydroxycyclohexyl(2-hydroxy-7,7-dimethylbicyclo[2.2.1]hept-1-ylmethyl)sulfonamido]-2-methyl-1,3-cyclohexanedicarboxylic acid, and stereoisomers thereof. Enantionmers of N,N-dicyclohexyl-(1S)-isoborneol-10-sulfonamide include (1S)-10-(N,N-dicyclohexylsulfamoyl) isoborneol and (1R)-10-(N,N-dicyclohexylsulfamoyl) isoborneol.

MT103 may be purchased from commercially available sources (e.g., ALDRICH, FLUKA, CAS number 99295-72-4) and may be synthesized as described in *Chiral auxiliary conferring excellent diastereodifferentiation in reactions of O-enoyl and enolate derivatives*, W. Oppolzer, Tetrahedron 43, 1969 (1987) and in W. Oppolzer and *Enantioselective systheses of—amino acids from* 10-*sulfonamido-isobornyl esters and di-t-butyl azodicarboxylate*, R. Moretti, Tetrahedron 44, 5541 (1988). Oppolzer taught the use of MT103 as an agent useful for making certain kinds of stereospecific chemicals. Other researchers have published work that describes MT103, and chemically modified derivatives of MT103, as compounds for stereochemical uses.

Figure 9:
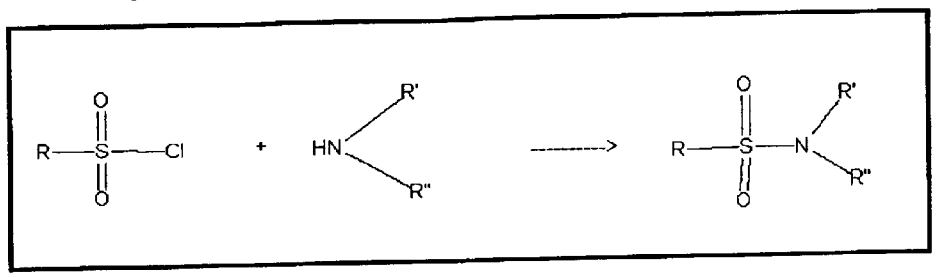
FIG. 9 depicts a chemical synthesis route for creating members of the MT103 family.

FIG. 9 depicts a reaction scheme for making sulfonamides that can be used to make the members of the MT103 family. Referring to FIG. 9, aryl or alkyl sulfonile chloride is reacted with a secondary amine in a single-step reaction. If the R, R', or R" contain amine, carboxylic, or hydroxylic groups, then protective groups are typically used to prevent the production of an excessive number of secondary products. Artisans of ordinary skill will be able to synthesize the variants of MT103 set forth herein, and other chemicals that are in the family of chemicals that share the features of MT103. References that address sulfonamide synthesis are, for example: Gong, B.; Zheng, C.; Skrzpczak-Jankun, E.; Yan, Y.; Zhang, J.; J. Am. Chem. Soc. 1998, 120, 11194–11195; Gong, B.; Zheng, C.; Zeng, H; Zhu, J., J. Am. Chem. Soc. 1999, 121, 9766–9767; Nuckolls C., Hof, F.; Martin, T.; Rebek J Jr.; J. Am. Chem. Soc. 1999, 121, 10281–10285; R. Ohme; H. Preuschhof. Liebigs Ann. Chem. 713, 74–86 (1968); Tetrahedron Letters, 38, 50, 8691–86 (1997); and Bermann, Manfred; Van Wazer, John R. Synthesis (1972), (10), 576–7.

Pharmaceutically acceptable salts of the compounds described herein may be synthesized according to methods known to those skilled in this art, see, for example Pharmaceutical Salts: Properties, Selection, and Use, P. Heinrich Stahl (Editor), Camille G. Wermuth (Editor) June 2002. Generally, such salts are prepared by reacting the free base forms of these compounds with a stoichiometric amount of the appropriate acid in water or in an organic solvent, or in a mixture of the two; generally, nonaqueous media like ether, ethyl acetate, ethanol, isopropanol, or acetonitrile are preferred. Lists of some appropriate salts are found, for example, in Remington's Pharmaceutical Sciences, 17th ed., Mack Publishing Company, Easton, Pa., 1985.

In some embodiments, the compounds described herein are used in combination with one or more potentiators and/or chemotherapeutic agents for the treatment of cancer or tumors. Examples and descriptions of potentiatiors and combination therapies are provided in, for example, U.S. Pat. Nos. 6,290,929 and 6,352,844.

The compounds described herein may be administered as a single active drug or a mixture thereof with other anti-cancer compounds, and other cancer or tumor growth inhibiting compounds. The compounds may be administered in oral dosage forms that include tablets, capsules, pills, powders, granules, elixirs, tinctures, suspensions, syrups, and emulsions. Further, the compounds may be administered in intravenous (bolus or infusion), intraperitoneal, subcutaneous, or intramuscular form.

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used.

Techniques and compositions for making dosage forms useful in the present invention are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.).

Suitable binders, lubricants, disintegrating agents, coloring agents, flavoring agents, flow-inducing agents, and melting agents may be included as carriers, e.g., for pills. For instance, an active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like.

Suitable binders include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, for example, starch, methyl cellulose, agar, bentonite, xanthan gum, and the like.

The compounds may also be used with liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds may also be coupled to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

The active compounds can be administered orally in solid dosage forms, such as capsules, tablets, and powders, or in liquid dosage forms, such as elixirs, syrups, and suspensions. The active compounds can also be administered parentally, in sterile liquid dosage forms.

Capsules may contain the active compound and powdered carriers, such as lactose, starch, cellulose derivatives, magnesium stearate, stearic acid, and the like. Similarly, such diluents can be used to make compressed tablets. Both tablets and capsules can be manufactured as immediate release products or as sustained release products to provide for continuous or long-term release of the active compounds. The deliverable form of the compounds can be sugar coated or film coated to mask any unpleasant taste and protect the tablet from the atmosphere, or enteric coated for selective disintegration in the gastrointestinal tract.

For oral administration as a liquid, the drug components may be combined with any oral, non-toxic, pharmaceutically acceptable inert carrier such as ethanol, glycerol, water, and the like. Examples liquid forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Liquid dosage forms may contain, for example, suitable solvents, preservatives, emulsifying agents, suspending agents, diluents, sweeteners, thickeners, and melting agents.

Liquid dosage forms for oral administration can contain coloring and flavoring, as needed. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds described herein may also be administered in intranasal form via use of suitable intranasal vehicles, or via transdermal routes, using those forms of transdermal skin patches known to those skilled in these arts. To be administered in the form of a transdermal delivery system, the dosage administration will generally be continuous rather than intermittent throughout the dosage regimen. Parenteral and intravenous forms may also include minerals and other materials to make them compatible with the type of injection or delivery system chosen.

The compounds set forth herein may also be used in pharmaceutical kits for the treatment of cancer, or other purposes, which comprise one or more containers containing a pharmaceutical composition comprising a therapeutically effective amount of the compound. Such kits may further include, if desired, one or more of various components, such as, for example, containers with the compound, containers with one or more pharmaceutically acceptable carriers, additional containers, and instructions. The instructions may be in printed or electronic form provided, for example, as inserts or labels, indicating quantities of the components to be administered, guidelines for administration, and/or guidelines for mixing the components.

Dosage levels from about 0.1 mg to about 100 mg of active compound per kilogram of body weight per day are preferable dosages. The amount of active compound that may be combined with the carrier materials to produce a single dosage form will vary depending upon the host treated and the particular mode of administration. Dosage unit forms will generally contain between from about 0.1 mg to about 1000 mg of an active compound. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy. For example, a suitable dosage adopted for oral or intravenous administration of a compound of the MT103 family may range from about 0.1 to about 1000 mg per dose, from 1 to 5 times daily.

The method of administration of the compounds set forth herein can be any suitable method that is effective in the treatment of the particular cancer or tumor type being treated. Treatment may be oral, rectal, topical, parenteral or intravenous administration or by injection into a tumor or cancer. The method of applying an effective amount also varies depending on the disorder or disease being treated. It is believed that parenteral treatment by intravenous, subcutaneous, or intramuscular application of the compounds set forth herein, formulated with an appropriate carrier, additional cancer inhibiting compound or compounds or diluent to facilitate application will be the preferred method of administering the compounds to mammals.

A topological computer modeling program that incorporates a molecular shape learning system has been used to identify the new family of drugs exemplified by MT103. The modeling program takes topological information about chemicals that are known to be effective anti-cancer drugs, and in a next step identifies common topological features that the drugs should share to show activity in the property under study. Then the program identifies new chemicals that have the common topological features. The program is designed not only to identify chemicals that are anti-cancer compounds but also to identify chemicals that are useful to combat specific types of cancer. MT103 was identified by the program as a chemical that would inhibit the growth of cancer cells. Further, MT103 was identified as a compound having particular efficacy against non-small lung cancer cells. The fact that a compound was successfully identified with that function is proof of the efficacy and utility of the compounds predicted by the computer model.

The computer modeling approach relies on molecular topology to determine physicochemical properties of molecules. The topological approach relies on mathematical means to describe and construct descriptive computer models. Through these models, it is possible to forward engineer specific structural activity relations of a molecular charge density alone or in response to adjacent electrotopological features. The topological approach accounts for the true structural invariant of a molecule that is not affected by vibrational or conformational changes. Aspects of this approach are set forth by Galvez in J. Gálvez et al., *J. Chem Inf. Comput. Sci.*, Vol. 34, No. 3, 1994; J. Gálvez et al., *J. Chem Inf. Comput. Sci.*, Vol. 34, No. 5, 1994; J. Gálvez et al., *J. Chem Inf. Comput. Sci.*, Vol. 35, No. 2, 1995; J. Gálvez et al., *Bioorganic & Medicinal Chemistry Letters*, Vol. 6, No. 19, 1996; J. Gálvez et al., *Journal of Molecular Graphics*, Vol. 14, 1996; J. Gálvez, *Journal of Molecular Structure* (Theochem), Vol. 429, 1998; J. V. de Julián-Ortiz, *Journal of Molecular Graphics and Modeling*, Vol. 16, 1998; Jesus V. de Julián-Ortiz et al., *Journal of Medicinal Chemistry*, Vol. 42, No. 17; Rafael Gozalbes et al., *Antimicrobial Agents and Chemotherapy*, Vol. 44, No. 10, October 2000; M. J. Duart et al., *Journal of Computer-Aided Molecular Design*, Vol. 15, 2001; L. Lahuerta Zamora et al., *Analytical Chemistry*, Vol. 73, No. 17, Sep. 1, 2001.

Trained models predict the bioactive topology of molecules and can be readily interpreted to guide the design of new active compounds. This approach combines three advances: a representation that characterizes surface shape such that structurally diverse molecules exhibiting similar surface characteristics are treated as similar; a new machine learning methodology that can accept multiple orientations and confirmations of both active and inactive molecules; and an iterative process that applies intermediate models to generate new molecular orientations to produce better predictive models. Two aspects of the program described above, the method of iterative reposing objects to produce better models and the method of training a model when each object has multiple representations, are applicable not only to biological activity modeling but also to other physicochemical characteristics.

The efficacy of the compounds generated by the topological computer modeling program can be confirmed using routine screening by using known cancer cell lines. Cell lines are available from NCI, American Tissue Type Culture, or other laboratories. The NCI has assembled a three cell-line test and a 60 cell-line test for identifying anti-cancer drugs (see M. R. Boyd and K. D. Paull, Some Practical Considerations and Applications of the NCI in vitro Drug Discovery Screen, Drug Dev. Res. 34:91109, 1995; M. R. Boyd, The NCI In Vitro Anticancer Drug Discovery Screen, Concept, Implementation, and Operation 1985–1995, In Drug Development: Preclinical Screening, Clinical trials and Approval, (Teicher, ed.) Totowa, N.J., Humana Press, 1997, pp. 23–42.

The following examples show that the MT103 family of compounds are effective general anti-cancer agents, and, moreover, that they have selectivity for non-small cell carcinoma cells. The topological computer modeling system described herein was used to generate chemical structures of drugs that are effective against non-small cell carcinoma cells, and MT103 was identified as a desirable anti-cancer drug. Subsequent testing by the independent governmental agency NCI provided further evidence that MT103 was a highly effective anti-cancer drug. Additional experiments with the NCI-H226 cell line provided further proof of the efficacy of MT103. The following examples are illustrative and not intended to be limiting of the invention.

EXAMPLES

Example 1

N,N-dicyclohexyl-(1S)-isoborneol-10-sulfonamide Predicted to be an Effective Anti-Cancer Agent by Topological Computer Modeling Table 1 shows the output for the topological computer model for selected anti-cancer agents and for N,N-dicyclohexyl-(1S)-isoborneol-10-sulfonamide. This output indicates that N,N-dicyclohexyl-(1S)-isoborneol-10-sulfonamide is an effective anti-cancer agent. As a control for the computer model, the computer model was also used to predict the results for known anti-cancer agents such as paclitaxel and topotecan, as well as for Ifosamide and Busulfan, agents that are typically not employed as anti-cancer agents. As indicated in Table 1, N,N-dicyclohexyl-(1S)-isoborneol-10-sulfonamide is predicted to be effective for multiple types of cancer, with a -logGI$_{50}$ value of at least 6.3 for each type of cancer that was tested.

TABLE 1

Topological computer model results for MT103 and selected anti-cancer compounds.

| Modeled Properties for Compounds | MT103 | Paclitaxel | Topotecan | Ifosamide | Busulfan |
|---|---|---|---|---|---|
| Activity against breast cancer NCI-MCF7 | >90%* | >90%* | >90%* | <10% probability | <10% probability |
| -log(GI$_{50}$), molar | 7.2 | 8.8 | 7.5 | <5 | <5 |

TABLE 1-continued

Topological computer model results for MT103 and selected anti-cancer compounds.

| Modeled Properties for Compounds | MT103 | Paclitaxel | Topotecan | Ifosamide | Busulfan |
|---|---|---|---|---|---|
| Activity against lung cancer NCI-H460 | >90%* | >90%* | >90%* | <10% probability | <10% probability |
| $-\log(GI_{50})$, molar | 6.3 | 7.4 | 7.6 | <5 | <5 |
| Activity against CNS cancer NCI-SF268 | >90%* | >90%* | >90%* | <10% probability | <10% probability |
| $-\log(GI_{50})$, molar | 7.3 | 7.6 | 7.0 | <5 | <5 |
| Protein Kinase C Inhibitor, Log Ki, nM | 0.9 | 0.1 | 2 | >4 | >4 |
| Induction of Apoptosis | 21% | 69% | 3.6% | 0% | 0% |

The pharmacokinetic properties of MT103 have been calculated and result in some predictions that show the usefulness of the chemical. The predictions indicate that MT103 will decay according to a 2 or 3 compartment model with a predicted terminal elimination half-life of about 3 hours. An average peak plasma concentration of about 1 mg/L should occur about an hour after dosing. The total clearance is estimated to be about 25 L/h and the mean apparent volume of distribution at steady state as about 1.5 L/kg. The expected mean oral bioavailabiliy of MT103 is about 20% and about 79% of the MT103 in the plasma is bound to protein in the body. Analogs having a structure similar to MT103 are expected to have similar pharmacokinetic properties.

Example 2

NCI Three Cell-Line Test Indicates That N,N-dicyclohexyl-(1S)-isoborneol-10-sulfonamide is an Effective Anti-cancer Agent This Example shows that MT103 is predicted by in vitro cell testing to be an effective anti-cancer agent. The testing in this Example was performed by NCI, as per their 3-cell line panel test. The results are reported as the percent of the growth of the treated cells compared to the untreated control cells. The criterion for being an effective compound and for being subjected to further testing is that the tested compound reduce the growth of any one of the three cell lines to approximately 32% or less. As shown in Table 2, MT103 was much more effective than the commonly accepted scientific accepted criterion; in fact, MT103 reduced the growth of all three cell lines to 16% or less at the one concentration tested.

TABLE 2

MT103 shown to be effective by NCI 3 cell-line test.

| | Growth, Percentage | | |
|---|---|---|---|
| Concentration of MT103 in growth medium | MCF7 Cell line (Breast Cancer) | NCI-H460 Cell Line (Non-Small cell Lung) | SF-268 Cell Line (Central Nervous System) |
| $1(10^{-4})$ Molar | 0 | 16 | 14 |

The methods for conducting the test are described below in Example 3, except that the cells were exposed to a single concentration of MT103, at $1 \times 10^{-4}$ Molar, and colorimetric determinations wear made with alamar blue (Biotechniques 21(5):780–782 (1996)).

Example 3

NCI Sixty Cell Line Test Shows that MT103 is an Effective Anti-cancer Drug

Figure 10:
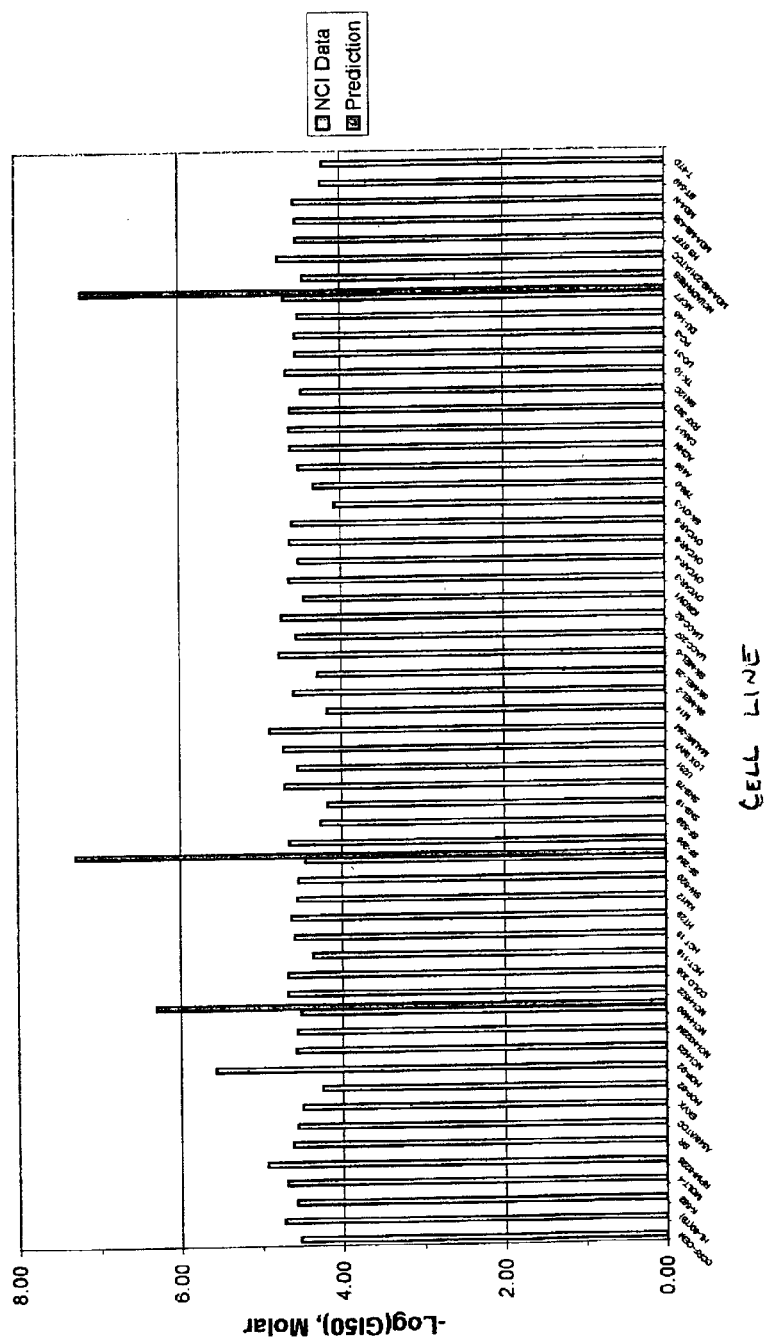
FIG. 10 depicts $GI_{50}$ values for MT103 for a variety of cell lines, with the $GI_{50}$ values being plotted as $-\log GI_{50}$.

The NCI tested MT103 with 60 cell lines, and reported the $GI_{50}$, TGI, and $LC_{50}$ values of MT103 for each cell line, see FIG. 10 and Table 3.

TABLE 3

NCI 60 cell-line test for the drug MT103.

| Panel/Cell Line | GI50 | TGI | LC50 |
|---|---|---|---|
| Leukemia | | | |
| CCRF-CEM | 2.97E-05 | >1.00E-04 | >1.00E-04 |
| HL-60 (TB) | 1.90E-05 | 8.33E-05 | >1.00E-04 |
| K-562 | 2.68E-05 | >1.00E-04 | >1.00E-04 |
| MOLT-4 | 2.06E-05 | >1.00E-04 | >1.00E-04 |
| RPMI-8226 | 1.18E-05 | 3.68E-05 | >1.00E-04 |
| SR | 2.38E-05 | >1.00E-04 | >1.00E-04 |
| Non-Small Cell Lung Cancer | | | |
| A549/ATCC | 2.83E-05 | >1.00E-04 | >1.00E-04 |
| EKVX | 3.13E-05 | 9.83E-05 | >1.00E-04 |
| HOP-62 | 5.75E-05 | >1.00E-04 | >1.00E-04 |
| HOP-92 | 2.75E-06 | 3.16E-05 | >1.00E-04 |
| NCI-H23 | 2.69E-05 | 8.31-E05 | >1.00E-04 |
| NCI-H322M | 2.73E-05 | >1.00E-04 | >1.00E-04 |
| NCI-H460 | 3.09E-05 | >1.00E-04 | >1.00E-04 |
| NCI-H522 | 2.15E-05 | 5.50E-05 | >1.00E-04 |
| Colon Cancer | | | |
| COLO 205 | 2.13E-05 | 4.98E-05 | >1.00E-04 |
| HCT-116 | 4.38E-05 | >1.00E-04 | >1.00E-04 |
| HCT-15 | 2.57E-05 | >1.00E-04 | >1.00E-04 |
| HT29 | 2.35E-05 | >1.00E-04 | >1.00E-04 |
| KM12 | 2.84E-05 | 9.73E-05 | >1.00E-04 |
| SW-620 | 2.88E-05 | >1.00E-04 | >1.00E-04 |
| CNS Cancer | | | |
| SF-268 | 3.58E-05 | >1.00E-04 | >1.00E-04 |
| SF-295 | 2.26E-05 | >1.00E-04 | >1.00E-04 |
| SF-539 | 5.46E-05 | >1.00E-04 | >1.00E-04 |
| SNB-19 | 6.80E-05 | >1.00E-04 | >1.00E-04 |
| SNB-75 | 1.95E-05 | 8.83E-05 | >1.00E-04 |
| U251 | 2.87E-05 | >1.00E-04 | >1.00E-04 |
| Melanoma | | | |
| LOX IMVI | 1.90E-05 | 3.95E-05 | 8.23E-05 |
| MALME-3M | 1.31E-05 | 4.44E-05 | >1.00E-04 |
| M14 | 6.78E-05 | >1.00E-04 | >1.00E-04 |
| SK-MEL-2 | 2.60E-05 | 6.77E-05 | >1.00E-04 |
| SK-MEL-28 | 5.07E-05 | >1.00E-04 | >1.00E-04 |

TABLE 3-continued

NCI 60 cell-line test for the drug MT103.

| Panel/Cell Line | GI50 | TGI | LC50 |
|---|---|---|---|
| SK-MEL-5 | 1.68E−05 | 3.61E−05 | 7.77E−05 |
| UACC-257 | 2.85E−05 | 9.53E−05 | >1.00E−04 |
| UACC-62 | 1.88E−05 | 4.65E−05 | >1.00E−04 |
| Ovarian Cancer | | | |
| IGROV1 | 3.48E−05 | >1.00E−04 | >1.00E−04 |
| OVCAR-3 | 2.30E−05 | 6.30E−05 | >1.00E−04 |
| OVCAR-4 | 3.02E−05 | >1.00E−04 | >1.00E−04 |
| OVCAR-5 | 2.37E−05 | 5.70E−05 | >1.00E−04 |
| OVCAR-8 | 2.53E−05 | >1.00E−04 | >1.00E−04 |
| SK-OV-3 | 8.32E−05 | >1.00E−04 | >1.00E−04 |
| Renal Cancer | | | |
| 786-0 | 4.63E−05 | >1.00E−04 | >1.00E−04 |
| A498 | 3.04E−05 | 9.07E−05 | >1.00E−04 |
| ACHN | 2.38E−05 | >1.00E−04 | >1.00E−04 |
| CAKI-1 | 2.35E−05 | 9.05E−05 | >1.00E−04 |
| RXF 393 | 2.42E−05 | 9.77E−05 | >1.00E−04 |
| SN12C | 3.30E−05 | >1.00E−04 | >1.00E−04 |
| TK-10 | 2.16E−05 | 9.02E−05 | >1.00E−04 |
| UO-31 | 2.80E−05 | 8.94E−05 | >1.00E−04 |
| Prostate Cancer | | | |
| PC-3 | 2.78E−05 | >1.00E−04 | >1.00E−04 |
| DU-145 | 3.05E−05 | >1.00E−04 | >1.00E−04 |
| Breast Cancer | | | |
| MCF7 | 2.06E−05 | 9.05E−05 | >1.00E−04 |
| NCI/ADR-RES | 3.49E−05 | >1.00E−04 | >1.00E−04 |
| MDA-MB-231/ATCC | 1.69E−05 | 4.71E−05 | >1.00E−04 |
| HS 578T | 2.90E−05 | >1.00E−04 | >1.00E−04 |
| MDA-MB-435 | 2.84E−05 | 9.88E−05 | >1.00E−04 |
| MDA-N | 2.71E−05 | >1.00E−04 | >1.00E−04 |
| BT-549 | 5.93E−05 | >1.00E−04 | >1.00E−04 |
| T-47D | 6.20E−05 | >1.00E−04 | >1.00E−04 |

Methodology:

The NCI conducted a test of the MT103 drug against 60 human cell lines, with a minimum of five concentrations of MT103 at 10-fold dilutions. A 48 hour continuous drug exposure was used, and a sulforhodamine B (SRB) protein assay was used to estimate cell viability and growth. The human tumor cell lines of the cancer screening panel were grown in RPMI 1640 medium containing 5% fetal bovine serum and 2 mM L-glutamine. Cells were inoculated into 96 well microtiter plates in 100 $\mu$L at plating densities ranging from 5,000 to 40,000 cells/well depending on the doubling time of individual cell lines. After cell inoculation, the microtiter plates are incubated at 37° C., 5% $CO_2$, 95% air, and 100% relative humidity for 24 h prior to addition of experimental drugs.

After 24 h, two plates of each cell line were fixed in situ with TCA, to represent a measurement of the cell population for each cell line at the time of drug addition (Tz). MT103 was solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 $\mu$g/ml gentamicin. Additional four, 10-fold or ½ log serial dilutions were made to provide a total of five drug concentrations plus control. Aliquots of 100 $\mu$L of these different drug dilutions were added to the appropriate microtiter wells already containing 100 $\mu$l of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 $\mu$l of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 $\mu$l) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 $\mu$l of 80% TCA (final concentration, 16% TCA). Using the seven absorbance measurements (time zero, (Tz), control growth, (C), and test growth in the presence of drug at the five concentration levels (Ti)), the percentage growth was calculated at each of the drug concentrations levels. Percentage growth inhibition was calculated as:

[(Ti−Tz)/(C−Tz)]×100 for concentrations for which Ti>/=Tz
[(Ti−Tz)/Tz]×100 for concentrations for which Ti<Tz.

Three dose response parameters were calculated for each experimental agent. Growth inhibition of 50% (GI50) was calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment was calculated from [(Ti−Tz)/Tz]×100=−50. Values were calculated for each of these three parameters if the level of activity is reached; however, if the effect was not reached or was exceeded, the value for that parameter was expressed as greater or less than the maximum or minimum concentration tested.

Example 4

N,N-dicyclohexyl-(1S)-isoborneol-10-sulfonamide is an Effective Inhibitor of the Cell Growth of the Cancerous Cell Line NCI-H226

Figure 11:
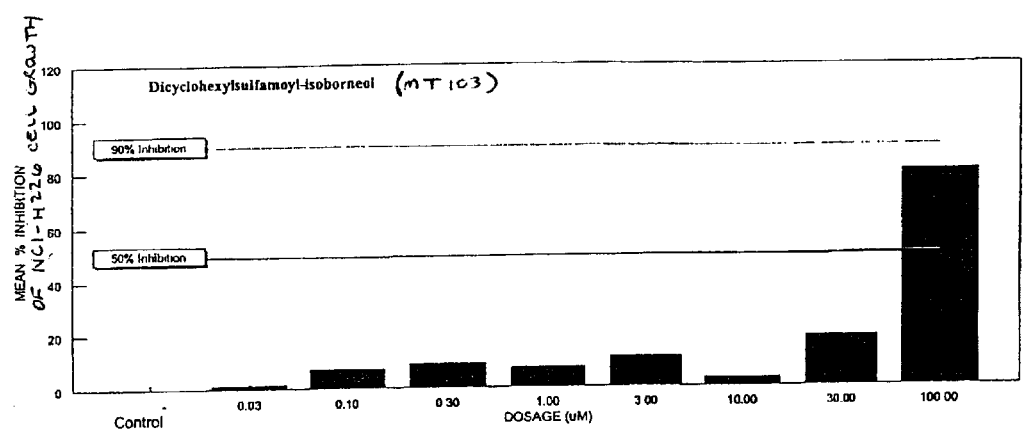
FIG. 11 depicts the inhibition of the NCI-H226 human non-small cell lung cancer cell line by MT103.

This Example shows that MT103 is a drug for treating human cancer, particularly non-small cell lung cancer. MT103 was tested with the NCI-H226 human non-small cell lung cancer cell line, and effectively inhibited growth of the cancer, see FIG. 11. The $GI_{50}$ for MT103 was 66 $\mu$M.

Methods

The MTS assay was employed in the evaluation of these compounds. The cells were harvested, centrifuged to remove the medium, and suspended in fresh complete medium. Samples were taken to determine cell density. The cell count was determined with a Coulter Model Z cell counter and viability was measured with propidium iodine staining call by analysis on Coulter EPICS flow cytometer. The cell line was plated at 5×10³ cells per well in complete medium. On the following day, the cells were closed with the dilutions of the compound. The plates were analyzed on Day for after initiation of treatment.

The cell line was propagated using standard tissue culture procedures and seeded in microtiter plates prior to dosing.

Control groups included a mock treatment, media control, and a positive control (doxorubicin, 1 μM). For each concentration level, eight replicates were treated. The cell line was propagated under sterile conditions at 37° C. in 5% $CO_2$ and 95% humidity. MT103 was stored at 4° C. until dissolved and diluted in complete medium.

Anti-cellular effects of the compound were assessed with the MTS dye conversion assay. MTS was purchased as a single solution, and stored at −20° C. Sample wells were treated with 20 microliters of the MTS solution and the plates were incubated for four hours at 37° C. to allow for conversion into the liquid soluble formazan product. The absorbance of formazan in each monolayer was measured at 490 nm on a Coulter microplate reader at four hours after addition of the MTS.

Example 5

Analogs of MT103 Determined to be Effective Therapeutic Agents

Results of the topological computer model showed that other members of the MT103 family are effective therapeutic agents. Table 4 shows compounds tested with the computer model and determined to be efficacious. MT103 is N,N-dicyclohexyl-(1S)-isoborneol-10-sulfonamide. Analog B is N-cyclohexyl-N-(3,4-dimethylcyclohexyl)-2,3-dihydroxy-7,7-dimethylbicyclo[2.2.1]heptylmethanesulfonamide. Analog C is N1-cyclohexyl-N1-{4-[(E)ethylidene]-3-methylenecycolhexyl}-1-(2-hydroxy-7,7-dimethylbicyclo[2.2.a]hept-1-yl)-1-ehtylenesulfonamide. Analog D is 4-cyclohexyl[1-(2-hydroxy-7,7-dimethylbicyclo[2.2.1]hept-1-yl)vinyl]sulfanamido-2-methyl-1,3 cyclohexanedicarboxylic acid. Analog E is 4-[3,4-dihydroxycyclohexyl(2-hydroxy-7,7-dimethylbicyclo[2.2.1]hept-1-ylmethyl)sulfonamido]-2-methyl-1,3-cyclohexanedicarboxylic acid.

| | Species of MT103 family tested by computer modeling and determined to be efficacious | | | | | |
|---|---|---|---|---|---|---|
| Compound | MT 103 | Analog A | Analog B | Analog C | Analog D | Analog E |
| Acetyl cholinesterase inhibitor | >90%* | >90%* | >90%* | >90%* | >90%* | >90%* |
| Peak time (hours) | 1 | 2 | 2 | 2 | 2 | 2 |
| Peak concentration (mg/L) | 1 | 0.04 | 2 | 1 | .1 | 0.4 |
| Metabolites (% of hepatic elimination) | 26 | 8 | 59 | 95 | 74 | 40 |
| Activity against breast cancer NCI-MCF7 (−log(GI50), molar) | >90%* (7.2) | >90%* (7.0) | >90%* (7.3) | >90%* (7.3) | >90%* (7.4) | >90%* (7.6) |
| Activity against lung cancer NCI-H460 (−log(GI50), molar) | >90%* (6.3) | >90%* (6.3) | >90%* (6.4) | >90%* (6.6) | >90%* (6.6) | >90%* (6.8) |
| Activity against CNS cancer NCI-SF268 (−log(GI50), molar) | YES (7.3) | YES (7.0) | YES (7.4) | YES (7.4) | YES (7.5) | YES (7.5) |
| Induction of apoptosis (%) | 21 | 25 | 40 | 40 | 31 | 35 |
| Log Ki (nM) for inhibitors of Protein Kinase-C | 0.9 | 1.5 | 0.8 | 1.0 | 1.0 | 0.5 |

*These percentages indicate calculated probabilities that the compound will have the indicated function.

The examples set forth herein are exemplary and are not intended to limit the scope or spirit of the invention. Patents, patent applications, journal articles, and publications that have been referenced in the application are hereby incorporated by reference herein.

What is claimed is:

1. A pharmaceutical composition comprising a unit dosage form comprising a pharmaceutically acceptable carrier or diluent containing a therapeutically effective amount for treatment of cancer in a patient of a chemical having the formula:

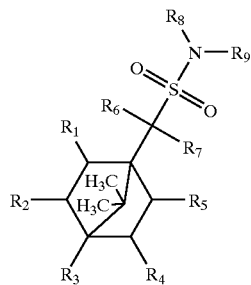

wherein $R_1$, $R_2$, $R_3$, $R_4$, and $R_5$ are independently chosen from the group consisting of H, OH, $C_1$–$C_3$ alkyl, a halogen, primary amine, secondary amine, tertiary amine, carboxy, alkoxy, alkyoxycarbonyl, carboxamido, and $C_1$–$C_3$ alkenyl;

wherein $R_6$ and $R_7$ are independently chosen from the group consisting of H, $C_1$–$C_3$ alkyl, and $C_1$–$C_3$ alkenyl; and, wherein $R_8$, and $R_9$ are independently chosen from the group consisting of chemical groups having 1 to 12 carbons;

or a pharmaceutically acceptable salt thereof.

2. The composition of claim 1 wherein $R_8$ and $R_9$ are independently chosen from the group consisting of $C_1$–$C_4$ alkyl, $C_1$–$C_4$ alkenyl, $C_3$–$C_6$ cycloalkyl, $C_3$–$C_6$ cycloalkenyl, and $C_6$ cycloalkyls derivitized with at least one member of the group consisting of $C_1$–$C_4$ alkyl, $C_1$–$C_4$ alkenyl, hydroxyl, and carboxyl.

3. The composition of claim 2 wherein at least one of $R_8$ and $R_9$ is $C_3$ alkyl.

4. The composition of claim 2 wherein at least one of $R_8$ and $R_9$ is methyl.

5. The composition of claim 2 wherein at least one of $R_8$ and $R_9$ is $C_6$ cycloalkyl and at least one of $R_8$ and $R^9$ is $C_6$ cycloalkyl derivitized with at least two methyls.

6. The composition of claim 2 wherein at least one $R_8$ and $R_9$ is $C_6$ cycloalkyl derivitized with at least two $C_1$–$C_2$ alkenyls and at least one of $R_6$ and $R_7$ is $C_1$–$C_2$ alkyl.

7. The composition of claim 6 wherein at least one of $R_8$ and $R_9$ is $C_6$ cycloalkyl.

8. The composition of claim 2 wherein at least one of $R_8$ and $R_9$ is $C_6$ cycloalkyl derivitized with at least one member of the group consisting of $C_1$–$C_3$ alkyl and carboxyl.

9. The composition of claim 8 wherein at least one of $R_8$ and $R_9$ is $C_6$ cycloalkyl and at least one of $R_6$ and $R_7$ is $C_1$–$C_2$ alkyl.

10. The composition of claim 2 wherein at least one of $R_8$ and $R_9$ is $C_6$ cycloalkyl derivitized with at least one hydroxyl.

11. The composition of claim 10 wherein at least one of $R_8$ and $R_9$ is $C_6$ cycloalkyl and at least one of $R_6$ and $R_7$ is $C_1$–$C_2$ alkyl.

12. The composition of claim 2 wherein and $R_8$ $R_9$ are independently chosen from the group consisting of $C_6$ cycloalkyl and $C_6$ cycloalkyls derivitized with at least one member of the group consisting of $C_1$–$C_4$ alkyl, $C_1$–$C_4$ alkenyl, hydroxyl, and carboxyl.

13. The composition of claim 12 wherein $R_6$ and $R_7$ are independently chosen from the group consisting of H and methyl.

14. A composition for administration to a cell, the composition comprising a unit dosage form comprising at least one therapeutic chemical in a pharmaceutically acceptable carrier, the therapeutic chemical having the formula:

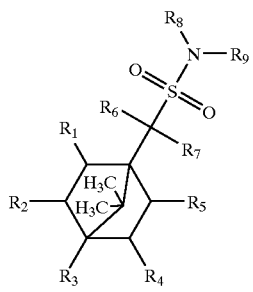

wherein $R_1$, $R_2$, $R_3$, $R_4$, and $R_5$ are independently chosen from the group consisting of H, OH, $C_1$–$C_3$ alkyl, a halogen, primary amine, secondary amine, tertiary amine, carboxy, alkoxy, alkyoxycarbonyl, carboxamido, and $C_1$–$C_3$ alkenyl;

wherein $R_6$ and $R_7$ are independently chosen from the group consisting of H, $C_1$–$C_3$ alkyl, and $C_1$–$C_3$ alkenyl; and wherein $R_8$ and $R_9$ are independently chosen from the group consisting of chemical groups having 1to 12 carbons;

or a pharmaceutically acceptable salt thereof.

15. The composition of claim 14 wherein the at least one chemical is chosen from the group consisting of N,N-dicyclohexyl-(1S)-isoborneol-10-sulfonamide, N,N-diisopropyl2-hydroxy-7,7-dimethylbicyclo[2.2.1]hept-1-ylmethanesulfonamide, N,N-dimethyl-2-hydroxy-7,7-dimethylbicyclo[2.2.1]hept-1-ylmethanesulfonamide, N-cyclohexyl-N-(3,4-dimethylcyclohexyl)-2,3-dihydroxy-7,7-dimethylbicyclo[2.2.1]hept-1-ylmethanesulfonamide, N1-cyclohexyl-N]-{4-[(E)ethylidone]-3-methylene-cycolhexyl}-1-(2-hydroxy-7,7-dimethylbicyclo[2.2.1]hept-1-yl)-1-ethylenesulfonamid; 4-cyclohexyl[(1-(2-hydroxy-7,7-dimethylbicyclo[2.2.1]hept-1-yl)vinyl]sulfanamido-2-methyl-1,3-cyclohexanedicaxboxylic acid, 4-[3,4-dihydroxycyclohexyl(2-hydroxy-7,7-dimethylbicyclo[2.2.1]hept-1-ylmethyl)sulfonamido]-2-methyl-1,3-cyclohexanedicarboxylic acid, and stereoisomers thereof.

16. The composition of claim 14 wherein the composition further comprises a second chemical having an anti-cancer activity upon exposure to the cell.

17. The composition of claim 14 wherein the composition further comprises a second chemical having apoptotic activity upon exposure to the cell.

18. The composition of claim 14 wherein the composition further comprises a second chemical that can act as an antagonist for hormones upon exposure to the cell.

19. The composition of claim 14 wherein the composition further comprises a second chemical having hypolipidemic activity upon exposure to the cell.

20. The composition of claim 14 wherein the composition further comprises a second chemical having antibacterial or antifungal activity upon exposure to the cell.

21. The composition of claim 1 wherein the pharmaceutically acceptable carrier or diluent comprises a binder, lubricant, disintegrating agent, coloring agent, flavoring agent, flow-inducing agent, melting agent, or a combination thereof.

22. The composition of claim 1 wherein the pharmaceutically acceptable carrier or diluent is a solid.

23. The composition of claim 22 wherein the composition is in a form of a capsule, tablet, or powder.

24. The composition of claim 1 wherein the composition is in a form for oral, rectal, topical, intravenous injection, or parenteral administration.

25. The composition of claim 1 wherein the pharmaceutically acceptable carrier or diluent is a liquid dosage form.

26. The composition of claim 25 wherein the composition is in a form of an elixir or syrup.

27. The composition of claim 14 wherein the pharmaceutically acceptable carrier or diluent comprises a binder, lubricant, disintegrating agent, coloring agent, flavoring agent, flow-inducing agent, melting agent, or a combination thereof.

28. The composition of claim 14 wherein the pharmaceutically acceptable carrier or diluent is a solid.

29. The composition of claim 28 wherein the composition is in a form of a capsule, tablet, or powder.

30. The composition of claim 14 wherein the composition is in a form for oral, rectal, topical, intravenous injection, or parenteral administration.

31. The composition of claim 14 wherein the pharmaceutically acceptable carrier or diluent is a liquid dosage form.

32. The composition of claim 31 wherein the composition is in a form of an elixir or syrup.

33. The composition of claim 14 wherein $R_8$ and $R_9$ are independently chosen from the group consisting of $C_1$–$C_4$ alkyl, $C_1$–$C_4$ alkenyl, $C_3$–$C_6$ cycloalkyl, $C_3$–$C_6$ cycloalkenyl, and $C_6$ cycloalkyls derivitized with at least one member of the group comprising of $C_1$–$C_4$ alkyl, $C_1$–$C_4$ alkenyl, hydroxyl, and carboxyl.

34. The composition of claim 33 wherein at least one of $R_8$ and $R_9$ is $C_3$ alkyl.

35. The composition of claim 14 wherein at least one of $R_8$ and $R_9$ is methyl.

36. The composition of claim 14 wherein at least one of $R_8$ and $R_9$ is $C_6$ cycloalkyl and at least one of $R_8$ and $R_9$ is $C_6$ cycloalkyl derivitized with at least two methyls.

37. The composition of claim 14 wherein at least one of $R_8$ and $R_9$ is $C_6$ cycloalkyl derivitized with at least two $C_1$–$C_2$ alkenyls and at least one of $R_6$, and $R_7$ is $C_1$–$C_2$ alkyl.

38. The composition of claim 14 wherein at least one of $R_8$ and $R_9$ is $C_6$ cycloalkyl.

39. The composition of claim 14 wherein at least one of $R_8$ and $R_9$ is $C_6$ cycloalkyl derivitized with at least one-member of the group consisting of $C_1$–$C_3$ alkyl and carboxyl.

40. The composition of claim 14 wherein at least one of $R_8$ and $R_9$ is $C_6$ cycloalkyl and at least one of $R_6$ and $R_7$ is $C_1$–$C_2$ alkyl.

41. The composition of claim 14 wherein at least one of $R_8$ and $R_9$ is $C_6$ cycloalkyl derivitized with at least one hydroxyl.

42. The composition of claim 14 wherein at least one of $R_8$ and $R_9$ is $C_6$ cycloalkyl and at least one of $R_6$ and $R_7$ is $C_1$–$C_2$ alkyl.

43. The composition of claim 14 wherein $R_8$ and $R_9$ are independently chosen from the group consisting of $C_6$ cycloalkyl and $C_6$ cycloalkyls derivitized with at least one member of the group consisting of $C_1$–$C_4$ alkyl, $C_1$–$C_4$ alkenyl, hydroxyl, and carboxyl.

44. The composition of claim 43 wherein $R_6$ and $R_7$ are independently chosen from the group consisting of H and methyl.

* * * * *